US010517563B2

(12) United States Patent
Kording et al.

(10) Patent No.: US 10,517,563 B2
(45) Date of Patent: Dec. 31, 2019

(54) ULTRASONIC DEVICE FOR DETECTING THE HEARTBEAT OF A PATIENT

(71) Applicant: UNIVERSITÄTSKLINIKUM HAMBURG-EPPENDORF, Hamburg (DE)

(72) Inventors: Fabian Kording, Hamburg (DE); Jin Yamamura, Hamburg (DE); Christian Ruprecht, Hamburg (DE); Kai-Kristoph Fehrs, Hamburg (DE)

(73) Assignee: UNIVERSITÄTSKLINIKUM HAMBURG-EPPENDORF, Hamburg (DE)

( * ) Notice: Subject to any disclaimer, the term of this patent is extended or adjusted under 35 U.S.C. 154(b) by 0 days.

(21) Appl. No.: 16/062,372

(22) PCT Filed: Dec. 15, 2016

(86) PCT No.: PCT/EP2016/081147
§ 371 (c)(1),
(2) Date: Jun. 14, 2018

(87) PCT Pub. No.: WO2017/102924
PCT Pub. Date: Jun. 22, 2017

(65) Prior Publication Data
US 2018/0368803 A1      Dec. 27, 2018

(30) Foreign Application Priority Data

Dec. 16, 2015   (EP) ..................................... 15200597

(51) Int. Cl.
*A61B 8/02*   (2006.01)
*A61B 5/00*   (2006.01)
(Continued)

(52) U.S. Cl.
CPC .............. *A61B 8/02* (2013.01); *A61B 5/0044* (2013.01); *A61B 5/055* (2013.01); *A61B 5/7292* (2013.01);
(Continued)

(58) Field of Classification Search
None
See application file for complete search history.

(56) References Cited

U.S. PATENT DOCUMENTS

| 5,032,793 A | 7/1991 | Yamamoto et al. |
| 2003/0195413 A1 | 10/2003 | Rubin et al. |

(Continued)

FOREIGN PATENT DOCUMENTS

| DE | 103 45 717 A1 | 4/2005 |
| DE | 10 2014 207985 A1 | 10/2016 |

OTHER PUBLICATIONS

International Written Opinion for International Application No. PCT/EP2016/081147 dated Mar. 20, 2017.
(Continued)

*Primary Examiner* — Carolyn A Pehlke
*Assistant Examiner* — Marjan Saboktakin
(74) *Attorney, Agent, or Firm* — Hunton Andrews Kurth LLP (57) ABSTRACT

An exemplary device for detecting a heartbeat of a patient can be provided which can include a transmitter which can provide ultrasonic waves, a receiver that can receive Doppler-shifted ultrasonic waves, and a hardware analyzer coupled to the receiver and which can evaluate a particular moment of the heartbeat of the patient based on a time-dependent signal obtained from the receiver. The hardware analyzer device can comprise a spectrum analyzer configured to extract time-varying frequency component(s) from the time-dependent signal provided by the receiver, and a
(Continued)

processing module which can evaluate the moment of the heartbeat based on a variation of at least one of the frequency components in time. The processing module can determine a window of interest (WOI) in time from the variation of the frequency component(s) in time, and the moment when the time-dependent signal provided by the receiver assumes a maximum within the WOI as the moment of the heartbeat.

21 Claims, 9 Drawing Sheets

(51) Int. Cl.
    *A61B 8/08*     (2006.01)
    *A61B 5/055*     (2006.01)
    *G01R 33/567*     (2006.01)
    *G01R 33/48*     (2006.01)
    *A61B 8/00*     (2006.01)
    *A61B 8/06*     (2006.01)
(52) U.S. Cl.
    CPC .......... *A61B 8/0883* (2013.01); *A61B 8/488* (2013.01); *G01R 33/4814* (2013.01); *G01R 33/5673* (2013.01); *A61B 5/7285* (2013.01); *A61B 8/06* (2013.01); *A61B 8/4494* (2013.01); *A61B 8/5223* (2013.01)

(56) References Cited

U.S. PATENT DOCUMENTS

| | | | |
|---|---|---|---|
| 2008/0015439 A1* | 1/2008 | Raju | A61B 8/02 600/455 |
| 2013/0178732 A1* | 7/2013 | Wedegaertner | A61B 5/033 600/413 |
| 2015/0094592 A1 | 4/2015 | Ravindran et al. | |

OTHER PUBLICATIONS

International Search Report for International Application No. PCT/EP2016/081147 dated Mar. 20, 2017.
Chris H.L. Peters et al. "Beat-to-beat detection of fetal heart rate: Doppler ultrasound cardiotocography compared . . . ," Phy. Measurement, vol. 25, No. 2 pp. 585-593 (Apr. 1, 2004).
Janusz Jezewski et al. "A novel technique for fetal heart rate estimation from Doppler ultrasound signal," Biomedical Engineering Online, vol. 10, No. 1 (Oct. 14, 2011).
Communication under Rule 71(3) EPC dated Sep. 20, 2019 for European patent application No. 16820218.2.

* cited by examiner

ULTRASONIC DEVICE FOR DETECTING THE HEARTBEAT OF A PATIENT

CROSS REFERENCE TO RELATED APPLICATION(S)

This application relates to, and claims the benefit and priority from International Patent Application No. PCT/EP2016/081147 filed on Dec. 15, 2016 that published as International Patent Publication No. WO 2017/102924 on Jun. 22, 2017, which claims the benefit and priority from European Patent Application No. 15200597.1 filed on Dec. 16, 2015, the entire disclosures of which are incorporated herein by reference in their entireties.

FIELD OF THE PRESENT DISCLOSURE

The present disclosure relates to an exemplary ultrasonic device for detecting the heartbeat of a patient that can preferably be used while the patient is being examined in an imaging apparatus, e.g., a magnetic resonance imaging (MRI) apparatus.

BACKGROUND INFORMATION

When the heart of a patient is examined using an MRI apparatus or other imaging apparatus, it is important to eliminate motion artifacts caused by the rapid motion of the heart. To date, the image acquisition of the MRI is synchronized to the moment of the patient's heartbeat using an external trigger signal. It is customary in the art to derive such a trigger signal from an electrocardiogram that is acquired simultaneously with the MRI imaging. The high magnetic and electromagnetic fields involved in the MRI imaging superimpose a rather high level of interference onto the weak electrical signals that have been picked up from the skin of the patient. In addition, electrolytes in the blood of the patient represent moving charges that generate even more interference in combination with the high magnetic field. This interference is termed magneto-hydrodynamic effect. Both types of interference deteriorate the detection of the heartbeat to the point where it can no longer serve as a reliable trigger signal for the MRI imaging. This causes the motion artifacts, which the triggering with the heartbeat was intended to avoid, to reappear in the resulting MRI images. In addition, when the heart of an unborn fetus is to be imaged using MRI, the skin of the fetus is not accessible for picking up an electrocardiogram, so no trigger signal for the MRI imaging is available at all.

To overcome these drawbacks certain publications (e.g., see, F. Kording, B. Schoennagel, G. Lund, F. Ueberle, C. Jung, G. Adam, J. Yamamura, "Doppler Ultrasound Compared with Electrocardiogram and Pulse Oximetry Cardiac Triggering: A Pilot Study", Magnetic Resonance in Medicine, doi: 10.1002/mm.25502 (2014)) propose, and demonstrate an MR-compatible cardiotocograph, CTG, to acquire the heartbeat of adult patients during MRI. The heart of the patient is examined with ultrasonic waves, and the reflected ultrasonic waves that are Doppler-shifted by the motion of the heart are detected. From this signal, the exact moment of the heartbeat is extracted using a wavelet-based peak detection. (See, e.g., J. Yamamura, I. Kopp, M. Frisch, R. Fischer, K. Valett, K. Hecher, G. Adam, U. Wedegartner, "Cardiac MRI of the Fetal Heart Using a Novel Triggering Method: Initial Results in an Animal Model", Journal of Magnetic Resonance Imaging 35, 1071-1076 (2012)) propose, and demonstrate on sheep, MRI imaging of a fetal heart that is triggered by a CTG signal. The Doppler frequency shift is proportional to the speed of movement of the heart; therefore, the Doppler-shifted ultrasonic signal can serve as a suitable triggering signal for the image acquisition in the MRI:

When the heart of a fetus is to be imaged using MRI, a high level of noise is superimposed on the CTG signal by the blood flow, breathing of the mother and by the MRI. As a robust trigger signal has to be processed in real-time without false negative or false positive trigger detections, there is therefore a need for an improved ultrasonic detection of the heartbeat during MRI.

SUMMARY OF EXEMPLARY EMBODIMENTS

To address at least such need, a device for detecting the heartbeat of a patient can be provided, according to an exemplary embodiment of the present disclosure. This exemplary device may preferably be used during imaging in or with the MRI apparatus because it can be very easily constructed to be MRI compatible. The basic exemplary operation of the exemplary device is not dependent on the presence of the MRI apparatus in any way. For example, the exemplary device can be used in conjunction with another type of imaging apparatus, such as computer tomography (CT) or positron emission tomography (PET) to provide the heartbeat of the patient as a trigger signal for the imaging. The slower the imaging method is compared with the rhythm of the heartbeat, the more the image quality is improved by the triggering. However, the device can be used even without any imaging taking place.

The exemplary device can comprise a transmitter for ultrasonic waves and a receiver for Doppler-shifted ultrasonic waves. The transmitter and the receiver may be implemented in one and the same transducer that performs both functions, but they may also be separate entities. Preferably, the transmitter and/or the receiver are piezoelectric transducers that may convert back and forth between an electrical signal and an ultrasonic signal.

The exemplary device further can comprise an evaluating module that is coupled to the receiver and configured to evaluate the moment $t_1$, $t_2$, $t_3$, $t_4$ of a heartbeat of the patient out of the time dependent signal from the receiver. This time dependent signal may be a raw signal, but it may also have been pre-processed in order to extract only a frequency component that has been Doppler-shifted from the frequency of the transmitter. This pre-processing may, for example, be accomplished using a demodulator.

The evaluating module can comprise a spectrum analyzer that is configured to extract at least one time-varying frequency component from the time-dependent signal delivered by the receiver. The evaluating module can further comprise a computer processing module that is configured to evaluate the moment $t_1$, $t_2$, $t_3$, $t_4$ of the heartbeat from the variation of at least one of the frequency components in time.

In an exemplary embodiment of the present disclosure, the device can comprise a configuration that can prevent coupling to the radio frequency field of the MRI at RF frequency $\omega_R$. Such configuration may, for example, comprise structures that are designed not to be resonant at the frequency $\omega_R$, the use of non-metallic materials, or standing wave traps configured to block the frequency $\omega_R$.

For example, a single heartbeat of the patient has been determined as an aperiodic event that generates a plurality of frequency components in the time-dependent signal from the receiver. However, the heartbeat is a periodically recurring event. Therefore, any frequency component generated by the heartbeat is a periodic function in time, with the period corresponding to the heart rate of the patient. This can be exploited to derive the moment $t_1$, $t_2$, $t_3$, $t_4$ of every single heartbeat from said function. Surprisingly, according to the exemplary embodiment of the present disclosure, this permits a very accurate detection of this moment $t_1$, $t_2$, $t_3$, $t_4$ even if the original time-dependent signal from the receiver is superimposed with noise that contains peaks about as high as, or even higher than, the peaks produced by the heartbeat. The only a priori knowledge used in this exemplary heartbeat detection is the fact that the heartbeat is a periodically recurring event.

Therefore, the variation of the frequency component in time that is evaluated by the computer processing module is mostly, e.g., a periodic variation that corresponds to the heart rate of the patient.

In one exemplary embodiment, the computer processing module may configure a computer processor to determine the moment $t_a$, $t_b$, $t_c$, $t_d$ where the at least one time-dependent frequency component assumes a maximum $m_a$, $m_b$, $m_c$, $m_d$ as the moment $t_1$, $t_2$, $t_3$, $t_4$ of the heartbeat. However, because the periodically varying frequency component more or less resembles a sine wave, its maximum may be a lot less sharp than a peak caused by the heartbeat in the original time-dependent signal from the receiver. To recover this sharpness and to improve the accuracy with which the moment $t_1$, $t_2$, $t_3$, $t_4$ can be detected, according to the invention, a hybrid detection of the heartbeat is used. The computer processing module can configure the computer processor to determine an exemplary window of interest (WOI) in time from the variation of the at least one frequency component in time. This window is subsequently used to determine the moment where the time-dependent signal from the receiver assumes a maximum $b_1$, $b_2$, $b_3$, $b_4$ within the WOI as the moment $t_1$, $t_2$, $t_3$, $t_4$ of the heartbeat. Thus, basically, a frequency component of the time-dependent signal is analyzed to determine a time frame that contains the desired heartbeat event, and this time frame is used to gate the actual detection of this event in the original signal in the time domain.

The WOI may be a window of pre-set length $\Delta t$ around the moment $t_a$, $t_b$, $t_c$, $t_d$ where the at least one time-dependent frequency component of the signal assumes a maximum $m_a$, $m_b$, $m_c$, $m_d$. In the alternative or in combination with this, the WOI may also be, for example, a window that extends between two moments $t_e$, $t_f$, $t_g$, $t_h$ where the at least one time-dependent frequency component (51a) assumes a minimum $m_e$, $m_f$, $m_g$, $m_h$.

For the detection of a fetal heart beat, multiple receivers may be used, entailing more electric wiring that is prone to pick up interference from the radio frequency field of the MRI. To reduce this interference and improve the compatibility of the device with MRI, resonant paths, especially circular closed conductive paths, should be avoided. Preferably, the response of the complete signal path from the receiver to the evaluating module at the frequency $\omega_R$ of the radio frequency field of the MRI is at least −30 dB lower than the response of a structure that is resonant at the frequency $\omega_R$. To this end, the inventors propose a further specially advantageous embodiment of the present disclosure that is directed at optimizing the electrical wiring in this way.

While this exemplary embodiment integrates well with the features relating to the evaluation of the signal described above, it is not tied in any way to this mode of evaluation.

In this exemplary embodiment, the device for detecting the heartbeat of a patient can comprise a transceiver unit with a transmitter for ultrasonic waves and a plurality of receivers for Doppler-shifted ultrasonic waves. The transmitters and the receivers may be one and the same element, for example, piezo-electric transducers that convert back and forth between an electrical voltage signal and an ultrasonic wave. The transceiver unit may therefore be a transducer unit. Each receiver has a first output terminal and a second output terminal. The transmitters and receivers may, for example, also be separate piezo-electric elements.

According to an exemplary embodiment of the present disclosure, each of the first output terminals of at least two receivers is connected by a branch line to a first common bus, and each of the second output terminals of the at least two receivers is connected by a branch line to a second common bus. Such exemplary topology of wiring can minimize or reduce the induction of radio frequency pulses to the common buses when the transceiver unit is used inside the radio frequency field of an MRI.

Likewise, multiple transmitters may be connected with common buses using the same topology. If transducers are used that combine the functions of a transmitter and a receiver in one single element, only one first common bus and one second common bus are necessary to wire all transducers. If the transducers are piezoelectric elements, each having a plus pole and a minus pole, then the first common bus may interconnect the plus poles, while the second common bus may interconnect the minus poles. The second common bus may also be connected to a ground potential.

The transmitter and the receivers may be mounted on a common dielectric substrate, preferably a flexible substrate. If the substrate is flexible, it may, for example, adapt to the shape of a mother's womb when placed on that womb. Exemplary mounting methods that are especially favorable for MRI compatibility are gluing and heat-sealing, which require no additional metal. For the device to be MRI-compatible, no ferromagnetic components may be introduced into the high magnetic field of the MRI, since it may heat up, and/or the magnetic field may apply a high force to it. It is very advantageous to use as little metal in the field of the MRI as possible, since the rapidly varying magnetic field of the MRI may cause eddy currents in metal. The magnetic field that is associated with these eddy currents disturbs the field of the MRI and causes artifacts. The imaging quality of the MRI strongly depends on the homogeneity of the magnetic field and on the ability of radio frequency pulses to propagate throughout the patient without being obstructed by metallic matter.

In another exemplary embodiment of the present disclosure, the dielectric substrate can be at least partially surrounded by a conductive shield. This conductive shield prevents external electromagnetic fields from being picked up by the first and/or second common bus to which the receivers are connected, in the manner of a Faraday cage. This is especially advantageous in MRI imaging, where the patient is interrogated with radio-frequency fields. For compatibility with MRI imaging, the shield should be made of a non-ferromagnetic but highly conductive material, such as copper, silver or gold. The shield may, for example, be a thin foil made of these metals. The shield may also, for example, comprise a non-conducting carrier, such as a plastic foil, carrying conductive structures.

The shield may surround the receivers in addition to surrounding the substrate. This improves the shielding of the first and second common buses at the price of introducing a slight mechanical damping of the ultrasonic waves captured by the receivers. If maximizing the coupling of the received ultrasonic waves to the receivers is more important, then the receivers may alternatively protrude out of the shield. In this case, the surface of the receivers that protrude out of the shield may comprise conductive structures that are electrically connected to the shield, so as to prevent electromagnetic waves from passing through the shield in the places where the receivers protrude out of the shield.

For example, at least part of the conductive shield is grounded. This grounding may be effected through the same cable that connects the first and second common buses to the outside world. For example, the cable may comprise at least two concentric conductors, wherein one conductor is connected to the first common bus and the other conductor is connected to the second common bus. At least a part of the conductive shield can be grounded via the outermost conductor of the cable. For example, the cable may be a coaxial cable. The grounded outer conductor then provides the ground potential to the second common bus as a reference potential for the signal acquisition, while at the same time providing the ground to the shield.

The cable may also be, for example, a triaxial cable. In this case, for example, the first common bus may be connected to the innermost conductor, the second common bus may be connected to the middle conductor, and the shield may connect the outermost conductor to ground. At the price of having one more conductor, this provides the freedom of arbitrarily choosing the reference potential for the signal detection.

For MRI imaging, it is important that the shield provides substantially no circular structures that may heat up or lead to image artifacts. Therefore, in a further specially advantageous embodiment of the present disclosure, at least part of the shield is divided into a plurality of segments. To make the different segments work together as one shield nonetheless, in a further specially advantageous embodiment of the present disclosure, at least two of the segments are electrically connected using a capacitor.

This capacitor can be dimensioned in a way that it blocks lower frequencies which are relevant for the generation of eddy currents within the shield, while being conductive for higher frequencies that may be picked up by the first and second common buses. In this manner, eddy currents are avoided, but the shield is effective for the frequencies that may obscure the measured signals.

In a further exemplary embodiment of the present disclosure, the first common bus and the second common bus can be arranged on different faces of the substrate, and/or the first common bus and the second common bus are interwoven along at least part of the signal path between at least one receiver and the spectrum analyzer. This exemplary configuration can reduce induced common-mode currents by the MRI and parasitic magnetic fields.

Preferably, the substrate (circuit board) is protected by a plastic casing that is biocompatible and sealed in a watertight manner.

When the heartbeat of a human fetus is to be detected, an additional challenge is that the fetus may move within the uterus so that its heart is no longer being examined by the ultrasonic waves from the transmitter. If this happens, the trigger signal for the MR imaging of the fetal heart is gone. Because the mother has to lie in a very uncomfortable position inside the MRI apparatus, which is not possible for an extended period of time, the loss of the trigger signal usually means that the whole examination of the fetal heart must be aborted and repeated at a later time. The intrauterine movement of the fetus may especially be triggered by the loud intimidating noise generated by the MRI.

To overcome this drawback, according to yet another exemplary embodiment of the present disclosure, the transceiver unit comprises a plurality of transmitters and/or receivers, and the evaluating arrangement/module can comprise tracking arrangement/module to determine which transmitters and/or receivers cover the present position of the heart of the patient, so that the Doppler-shifted ultrasonic waves can be registered by at least one receiver and evaluated by the evaluating module. The transmitters may, for example, be arranged in groups, and they may be activated either by group or individually. The transmitters, and/or the receivers, may, for example, be distributed over a large area in which a fetus is expected to be moving. For example, the transmitters and/or the receivers can be arranged on a flexible mat that can be placed on the mother's womb, so that every point in the uterus where the fetal heart can be is covered by at least one transmitter and/or receiver. Therefore, a constant detection of the heartbeat of the fetus, and thus a continuous trigger signal for the MRI, will be available, no matter which way the fetus moves.

For example, the evaluating module can comprise a feedback module that can control operation of the plurality of transmitters, whereas the feedback module can be configured to power on only those transmitters that have been identified to cover the present position of the heart of the patient by the tracking arrangement/module. No unnecessary ultrasound, which could result in artifacts, is then transmitted.

In a further exemplary embodiment of the present disclosure, the signal path between at least one receiver and the spectrum analyzer can comprise at least one standing wave trap configured to block the radio frequency $\omega_R$ of the MRT apparatus, and/or to prevent coupling between the signal path and the radio frequency $\omega_R$ of the MRI. This exemplary configuration avoids the introduction of common-mode signals into the wiring and avoids potential heating of the wire. Such heating could injure the patient by burning of the skin, or it might even be a fire hazard. Furthermore, the MRI image may be significantly disturbed, if the transmitted radio frequency $\omega_R$ of the MRI is induced into the signal path.

For example, the standing wave trap is formed from a coaxial cable with an inner conductor and an outer conducting shield. This may especially be the same coaxial cable that is carrying the signal. The coaxial cable is wound to a coil so that a first coil is formed in the inner conductor and a second coil is formed in the conducting shield. The second coil in the outer conducting shield is bridged by a capacitor that forms the standing wave trap in combination with said second coil in the outer conducting shield.

Moreover, if several piezo-electric elements are used, for example on a flexible substrate to create a large area for signal reception, multiple signals paths may be used. The signals paths may also couple to the radio frequency of the MRI, which has to be prevented in order to prevent heating of the signal paths and MRI image artifacts. This may especially be achieved by resonant parallel circuits, consisting of a parallel capacitor and inductor, tuned to the resonant frequency of the MRI, which are placed within each signal path.

In a still another exemplary embodiment of the present disclosure, the signal path between at least one receiver and the spectrum analyzer can comprise a plurality of standing wave traps, so that in the radio frequency $\omega_R$ field of the MRI apparatus, the signal travels no more than a quarter of the wavelength $\lambda$ corresponding to said radio frequency $\omega_R$ before traversing a first or a further standing wave trap. The magnetic field inside the MRI apparatus is very inhomogeneous and may result in localized heating of wiring.

If any currents coupled into the wiring by the radio frequency field cannot travel any further than λ/4 and if these are minimally attenuated by −30 dB, the heating and corresponding image artifacts can be effectively avoided.

For example, the signal path between at least one receiver and the spectrum analyzer can comprise a bandpass filter that rejects both the switching frequency $\omega_G$ of the gradient field of the MRI apparatus and the radio frequency $\omega_R$ of the MRI apparatus. The switching frequency $\omega_G$ is on the order of 200 kHz or below, while the frequency of the ultrasonic waves used to examine the heart of the patient is on the order of 1 MHz, and the radio frequency $\omega_R$ is on the order of 64 MHz and above. The bandpass may be preferably centered on the frequency of the ultrasonic waves. The width of the bandpass filter needs to be at least large enough to accommodate both the frequency of the transmitted ultrasonic wave and the frequency of the received ultrasonic wave with the maximum possible Doppler shift.

At least part of the evaluating module can be shielded by a housing that comprises conductive carbon fiber. While such a housing serves as a Faraday cage like a metallic housing, the generation of eddy currents and associated parasitic magnetic fields is greatly reduced.

In yet another exemplary embodiment of the present disclosure, a system can be provided that can comprise the MRI apparatus and a device for detecting the heartbeat of a patient according to the present disclosure. The trigger input of the MRI apparatus that triggers image acquisition is coupled to the determining arrangement/module of the exemplary device to receive the moment $t_1$, $t_2$, $t_3$, $t_4$ of the heartbeat of the patient, so that image acquisition is triggered at this moment $t_1$, $t_2$, $t_3$, $t_4$. The improved precision of the heartbeat detection and the improved resilience of this detection to interference of the MRI makes the triggering of the image acquisition more reliable. The reliability of the triggering in turn improves the quality of the final MR image. In addition, the triggering is also resilient against intra-uterine movement of the fetus, so that this movement no longer results in the MRI examination being aborted.

In yet another exemplary embodiment of the present disclosure, the following Examples can be provided:

Example 1

A device for detecting the heartbeat of a patient, preferably during imaging in a magnetic resonance imaging, MRI, apparatus or other imaging apparatus, comprising a transmitter for ultrasonic waves, a receiver for Doppler-shifted ultrasonic waves, and the evaluating arrangement/module coupled to the receiver and configured to evaluate the moment $t_1$, $t_2$, $t_3$, $t_4$ of a heartbeat of the patient out of the time-dependent signal from the receiver, wherein the evaluating arrangement/module comprise:
- a spectrum analyzer configured to extract at least one time-varying frequency component from the time-dependent signal delivered by the receiver; and
- a determining arrangement/module configured to evaluate the moment $t_1$, $t_2$, $t_3$, $t_4$ of the heartbeat from the variation of at least one of the frequency components in time.

Example 2

The exemplary device according to Example 1, wherein the determining module can configure a computer processor to determine the moment $t_a$, $t_b$, $t_c$, $t_d$ where the at least one time-dependent frequency component assumes a maximum $m_a$, $m_b$, $m_c$, $m_d$ as the moment $t_1$, $t_2$, $t_3$, $t_4$ of the heartbeat.

The aspects described above and further aspects, features and advantages of the present disclosure may also be found in the exemplary embodiments which are described in the following with reference to the appended drawings and claims.

BRIEF DESCRIPTION OF THE DRAWINGS

Further exemplary embodiments of the present disclosure are detailed in the description of the Figures, where this description shall not limit the scope of the present disclosure. The Figures show.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

Figure 1:
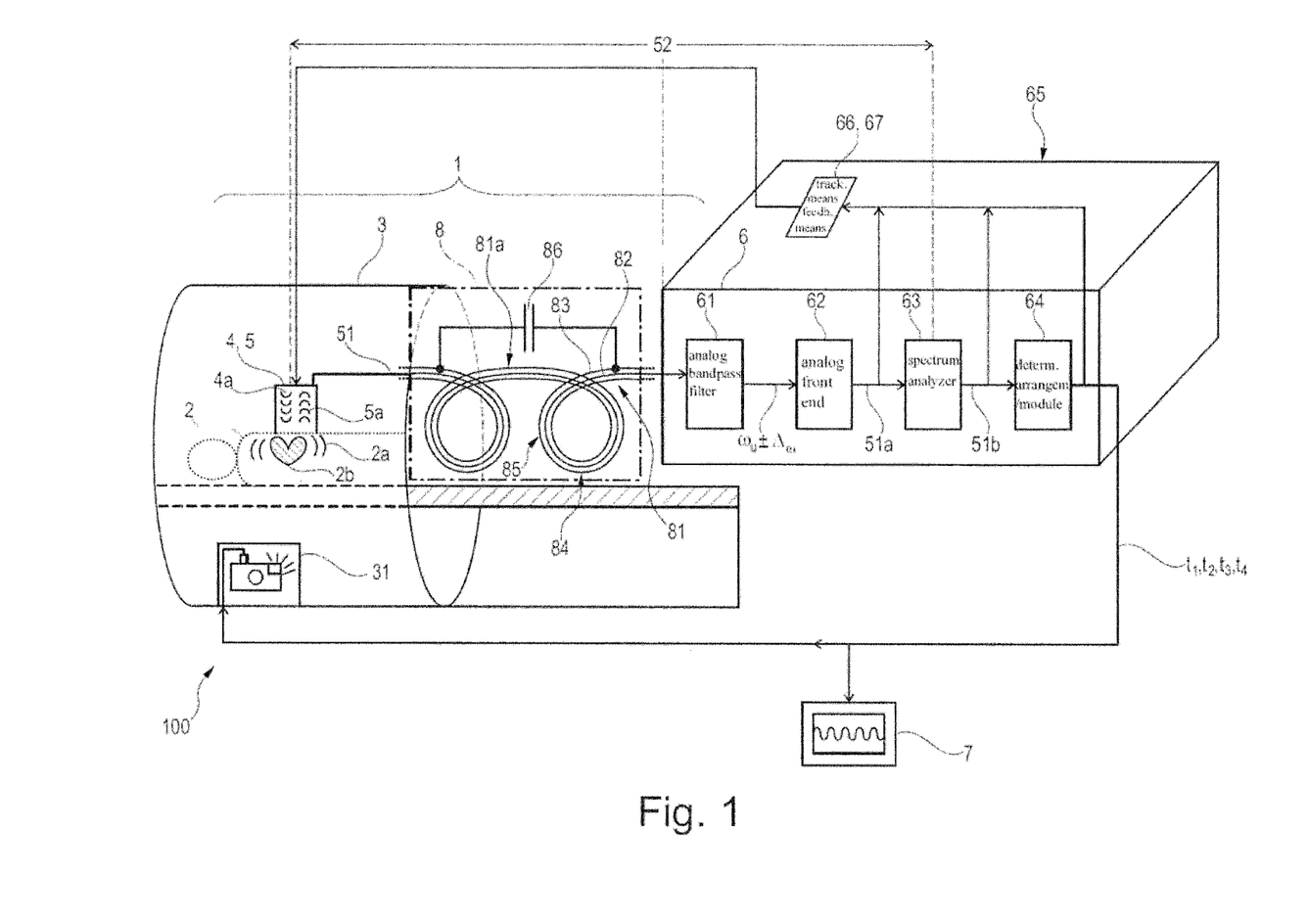
FIG. 1: exemplary embodiment of the device 1 and of the system 100 according to the present disclosure.

FIG. 1 shows a diagram of an exemplary embodiment of a device 1 for detecting the heartbeat 2a of a patient 2 to synchronize the data acquisition of an MRI apparatus 3. The patient 2 is located within the MRI apparatus 3, where his heart 2b is to be imaged. To trigger this imaging, the device 1 is used. The exemplary device 1 comprises a transmitter 4 for ultrasonic waves 4a and a receiver 5 for Doppler-shifted ultrasonic waves 5a. The transmitter 4 and the receiver 5 are integrated in one single component 4, 5. The time-dependent signal 51 from the receiver 5 is fed into the evaluating module/arrangement 6 via of a coaxial cable 81 with an inner conductor 82 and an outer conductive shield 83. A stretch of this coaxial cable 81 is wound into a coil 81a, thereby forming a first coil 84 in the inner conductor 82 and a second coil 85 in the outer conducting shield 83. The second coil 85 in the outer conducting shield 83 is bridged by a capacitor 86, so that this second coil 85 and the capacitor 86 together form a standing wave trap 8 that is part of the device 1. The resonance frequency of the standing wave trap 8 is set to the radio frequency $\omega_R$ of the MRI apparatus 3.

The evaluating module/arrangement 6 can be shielded in a housing 65 that comprises conductive carbon fiber, so that the generation of eddy currents and associated magnetic fields is reduced. The time-dependent signal 51 contains interference from two sources in the MRI apparatus 3, namely from the switching of the gradient fields at the frequency $\omega_G$ and from the radio frequency pulses with frequency $\omega_R$. To eliminate both sources of interference, the signal 51 is first filtered using an analog bandpass filter 61 that only lets a frequency band $\omega_U \pm \Delta \omega$ pass, wherein $\omega_U$ is the frequency of the transmitted ultrasonic waves 4a and $\Delta \omega$ is the Doppler shift that the received ultrasonic waves 5a have experienced due to the fast motion of the heart 2b of the patient 2. The signal 51 then passes through an analog front-end 62 that receives amplifies, demodulates and filters the signal 51 again, hence only signals with the frequency components of the Doppler shift $\Delta \omega$ remain in the signal 51a. The demodulation may also be performed in the digital domain.

The filtered signal 51a then passes through spectrum analyzer 63 that decomposes it into frequency components. Since a single heartbeat 2a of the patient 2 is an aperiodic event that is periodically recurring with a period corresponding to the heart rate of the patient 2, some frequency components 51b will be periodically time-varying with the same period. These frequency components are evaluated further by the determining module/arrangement 64 to yield the moment $t_1$, $t_2$, $t_3$, $t_4$ of the heartbeat 2a of the patient 2. By contrast, frequency components in the signal 51a that result from noise or spontaneous movement are not periodic and can be neglected. The signal path from the receiver 5 to the input of the spectrum analyzer 63 is labeled 52.

The filtered signal 51a, the time-varying frequency components 51b and the moment $t_1$, $t_2$, $t_3$, $t_4$ of the heartbeat are fed into tracking module/arrangement 66 that monitors whether the heart 2b of the patient 2 is still in range of the transceiver 4, 5. If the heart 2b has left this range, so that the heartbeat 2a can no longer be detected, the feedback module/arrangement 67 that is combined with the tracking module/arrangement 66 powers this transceiver 4, 5 off and powers on a different transceiver 4, 5 that covers the new position of the heart 2b, so that the detection of the heartbeat 2a can be resumed.

The moment $t_1$, $t_2$, $t_3$, $t_4$ of the heartbeat 2a is delivered to a display unit 7 where it can be directly monitored by the attending physician. The main purpose of the evaluated moment $t_1$, $t_2$, $t_3$, $t_4$ of the heartbeat 2a, however, is to serve as a trigger signal for the imaging in the MRI apparatus 3. To this end, the moment $t_1$, $t_2$, $t_3$, $t_4$ of the heartbeat 2a is fed into a trigger port 31 of the MRI apparatus 3 via a standard cable connection or via a wireless connection. A wireless connection has the additional benefit that it cannot create any ground loops. For the same reason, the evaluating module/arrangement 6 is battery-powered.

Figure 2:
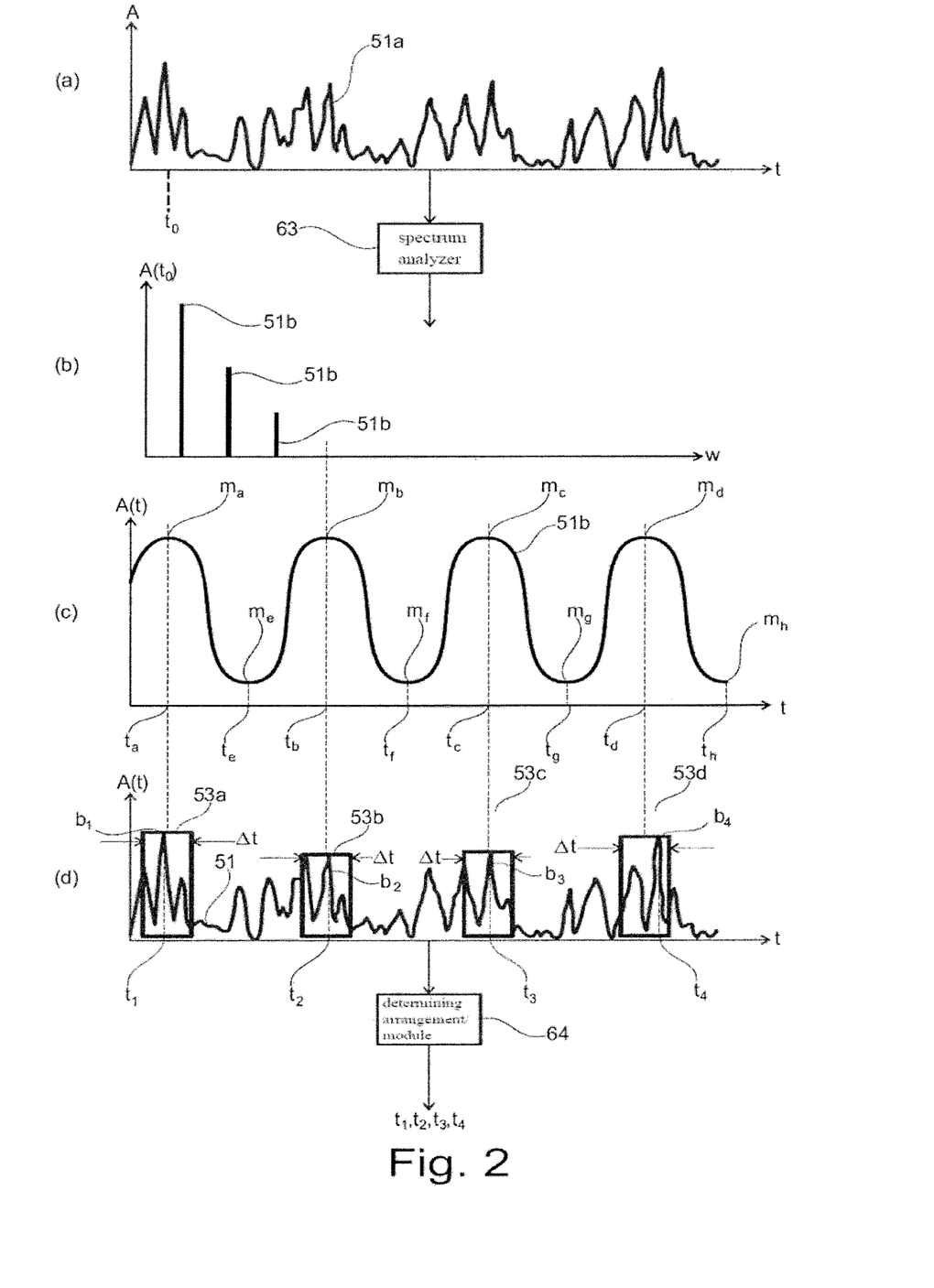
FIG. 2: an exemplary extraction of the moment $t_1$, $t_2$, $t_3$, $t_4$ of the heartbeat 2a out of the time-dependent signal 51 from the receiver 5.

FIG. 2 illustrates the extraction of the moment $t_1$, $t_2$, $t_3$, $t_4$ of the heartbeat 2a from the time-dependent filtered signal 51a in more detail. Diagram (a) shows the amplitude A of the filtered Doppler signal 51a over the time t. From this raw signal, the spectrum analyzer 63 extracts frequency components 51b with a time-varying amplitude A. To this end, the signal 51a is decomposed into frequency components at sampling time t, and it is monitored which of those frequency components vary in time. Diagram (b) shows the decomposition of the signal 51a into frequency components 51b at one point in time $t_0$. The decomposition can be done by discrete Fast Fourier Transform (FFT), filter banks or any other appropriate way.

Diagram (b) in FIG. 2 shows only those frequency components 51b that are time-varying, with amplitudes $A(t_0)$ that correspond to the spectral power density of the respective frequency components 51b. It should be noted that frequency components caused by noise may well have amplitudes $A(t_0)$ that are at least as large, or even larger, than the amplitudes $A(t_0)$ of the time-varying frequency components 51b. However, according to the present disclosure, the frequency components of the noise can be easily dismissed because they are not time-varying periodically and they are time-varying in the range of >3 Hz, whereas the range of the heartbeat is <2.5 Hz.

Diagram (c) in FIG. 2 shows the variation in time of the amplitude A(t) of one time-varying frequency component 51b. Within the range of diagram (c), the amplitude A(t) assumes four maxima $m_a$, $m_b$, $m_c$ and $m_d$ at times $t_a$, $t_b$, $t_c$ and $t_d$, respectively. The amplitude A(t) also assumes four minima $m_e$, $m_f$, $m_g$ and $m_h$ at times $t_e$, $t_f$, $t_g$ and $t_h$.

As shown in diagram (d) in FIG. 2, windows of interest 53a, 53b, 53c and 53d in time are generated from the times $t_a$, $t_b$, $t_c$ and $t_d$ at which the amplitude A(t) assumes a maximum in diagram (c). Each window 53a, 53b, 53c and 53d has a fixed length $\Delta t$. Within each window 53a, 53b, 53c and 53d, the determining module/arrangement 64 examines the original time-dependent signal 51a for the occurrence of the highest maximum. In each of the windows 53a, 53b, 53c and 53d, this maximum occurs at times $t_1$, $t_2$, $t_3$ and $t_4$ with amplitude A(t) values $b_1$, $b_2$, $b_3$ and $b_4$, respectively. It represents the E wave and is followed by a smaller maximum that represents the A wave. The times $t_1$, $t_2$, $t_3$ and $t_4$ are the final outcome of the determining module/arrangement 64. The data analyzed in FIG. 2 were acquired on an adult patient.

Figure 3:
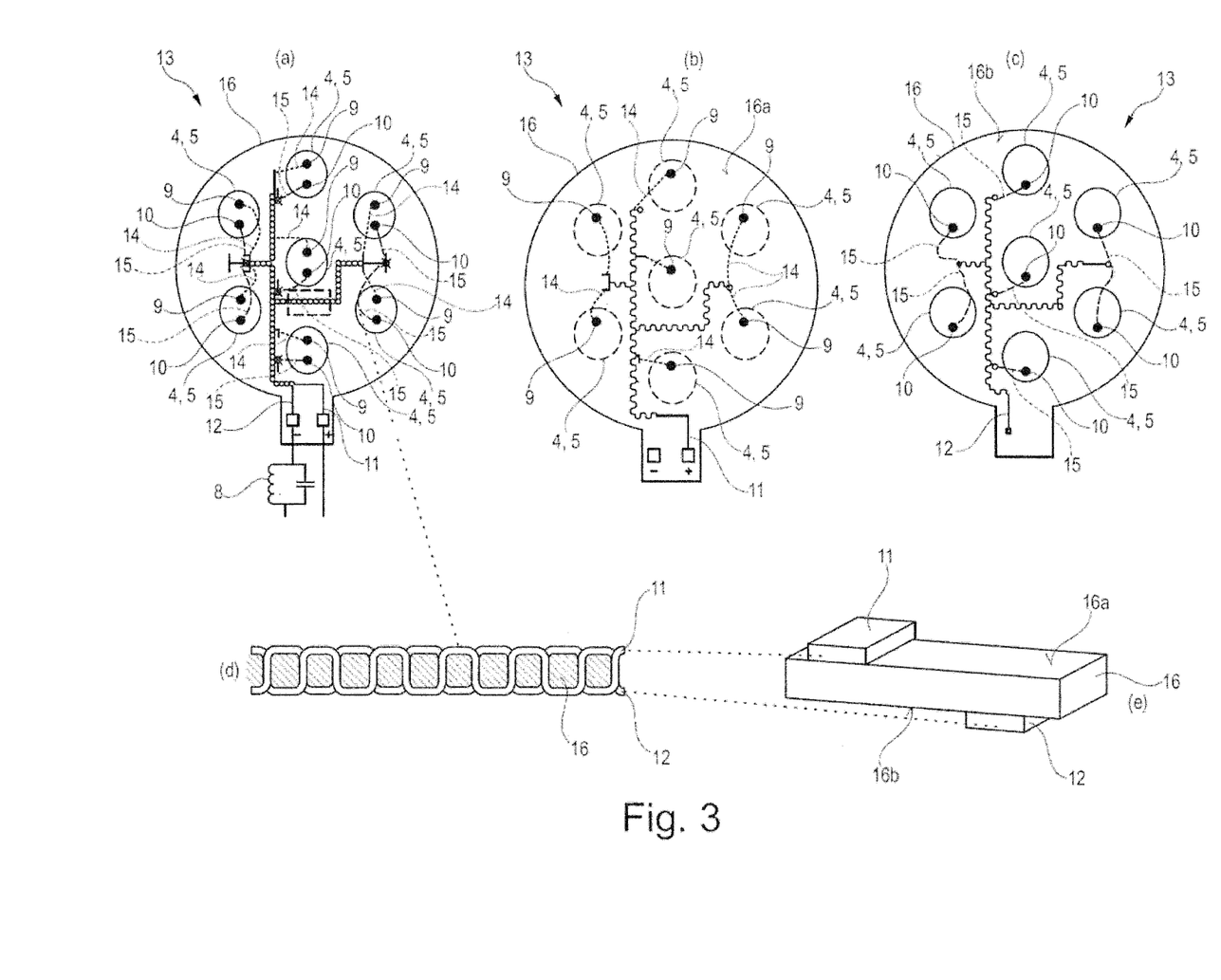
FIG. 3: a transceiver unit 13, optimized for compatibility with the MRI apparatus 3.

FIG. 3 details a transceiver unit 13 that is optimized for compatibility with the MRI apparatus 3. This embodiment is adapted for detection of the heartbeat 2a of a fetus 2, but it has no compensation for intra-uterine movement of the fetus 2. The transceiver unit 13 comprises a substrate 16 with an upper face 16a and a lower face 16b. Sub-figure (a) shows the components visible on both faces 16a and 16b of the substrate 16. Sub-figure (b) only shows the components visible on the upper face 16a, with the exception of the transceivers 4, 5 that are mounted on the lower face 16b, but shown in sub-figure (b) with dashed contours for clarity. Sub-figure (c) only shows the components visible on the lower face 16b.

Each transceiver 4, 5, which combines the function of a transmitter 4 for ultrasonic waves 4a and the function of a receiver 5 for Doppler-shifted ultrasonic waves 5a, has a first terminal 9 and a second terminal 10. The first terminals 9 are connected by branch lines 14 to a first common bus 11. The second terminals 10 are connected by branch lines 15 to a second common bus 12. The first terminals 9 and the branch lines 14 are all on the upper face 16a of the substrate 16, while the second terminals 10 and the branch lines 15 are all on the lower face 16b of the substrate 16.

The first terminals 9 of the transceivers 4, 5 are positive (plus) terminals, while the second terminals 10 of the transceivers 4, 5 are negative (minus) terminals. The second common bus 12 that interconnects the second terminals 10 is connected via a standing wave trap 8 to the outside world.

As shown in a sectional view in sub-figure (d), and in sub-figure (e) in a perspective view, both common buses 11 and 12 straddle the substrate 16 and are interwoven with each other. This arrangement of the wiring contains as few symmetries and circular structures as possible, so that both the coupling of radio frequency pulses into the buses 11 and 12 and the generation of parasitic magnetic fields by the currents flowing through the buses 11 and 12 are minimized.

Figure 4:
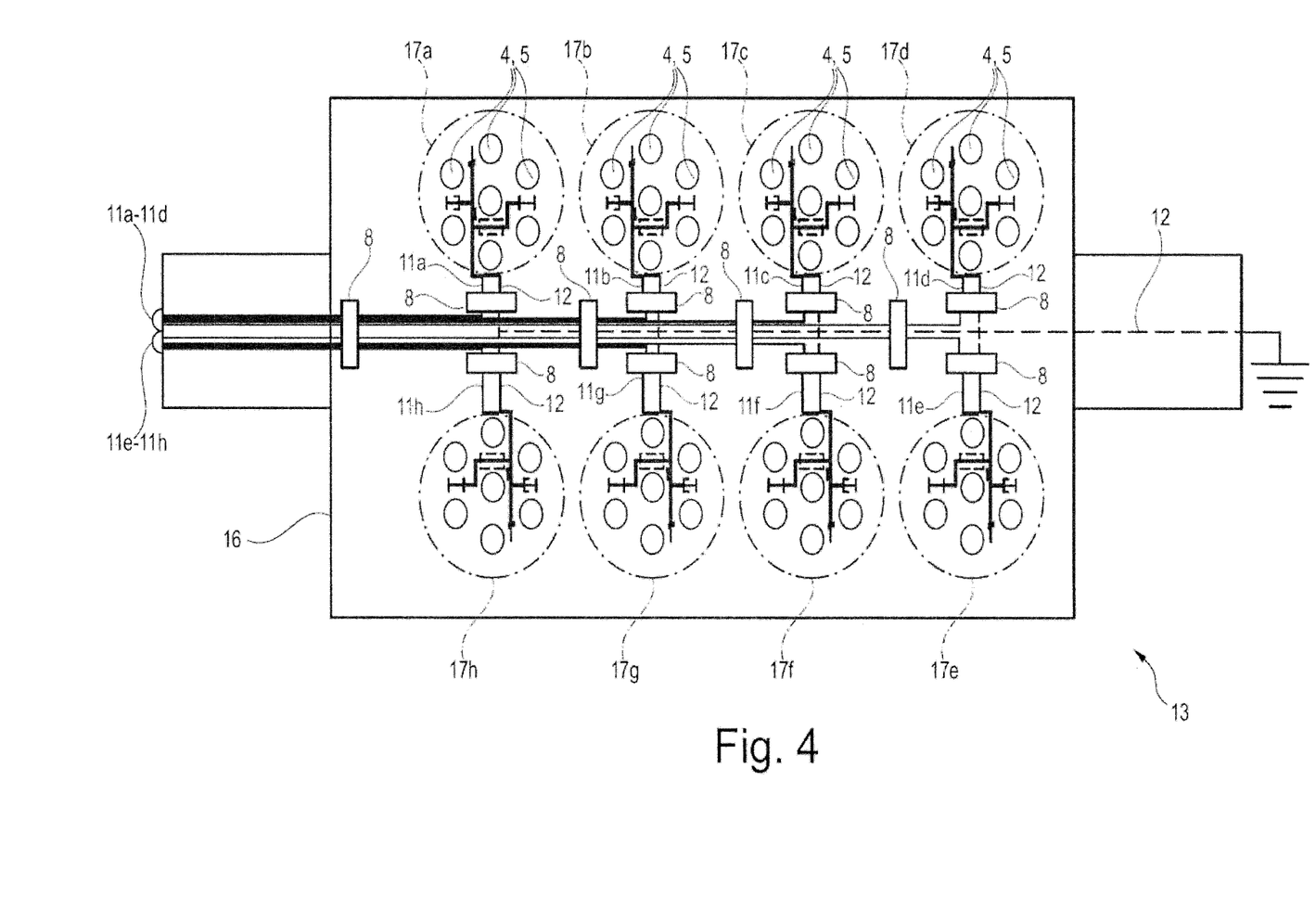
FIG. 4: a transceiver unit 13, further optimized for tracking of intra-uterine movement of a fetus.

FIG. 4 shows another embodiment of a transceiver unit 13 that is specifically adapted to compensate intra-uterine movement of a fetus 2 during an MRI examination. The substrate 16 is a large flexible mat designed to adapt to the shape of a mother's womb 2c. The transceivers 4, 5 are arranged in a plurality of groups 17a-17h, but may also be arranged individually. Even if transceivers are arranged in groups, their transmitting functions may be activated individually, and their receivers may be read out individually. In this grouped example, each group 17a-17h has a separate first common bus 11a-11h that connects the first terminals 9 of all transceivers 4, 5 in the group 17a-17h. All groups 17a-17h share one second common bus 12 that is connected to a ground potential. Every group 17a-17h has its own standing wave trap 8 through which all signals leaving this group 17a-17h on both buses 11a-11h, 12 have to pass. On its further path in the horizontal direction in the perspective of FIG. 4, the signals have to pass further standing wave traps 8. The standing wave traps 8 are arranged so that no signal can travel more than one quarter of the wavelength corresponding to the radio frequency $\omega_R$ of the MRI apparatus 3 without hitting the first or another standing wave trap 8. This ensures that no matter where on the extended substrate 16 a radio frequency pulse couples into some wiring, this will not cause a potentially dangerous local heating of this wiring and will reduce MRI related image artifacts.

Figure 5:
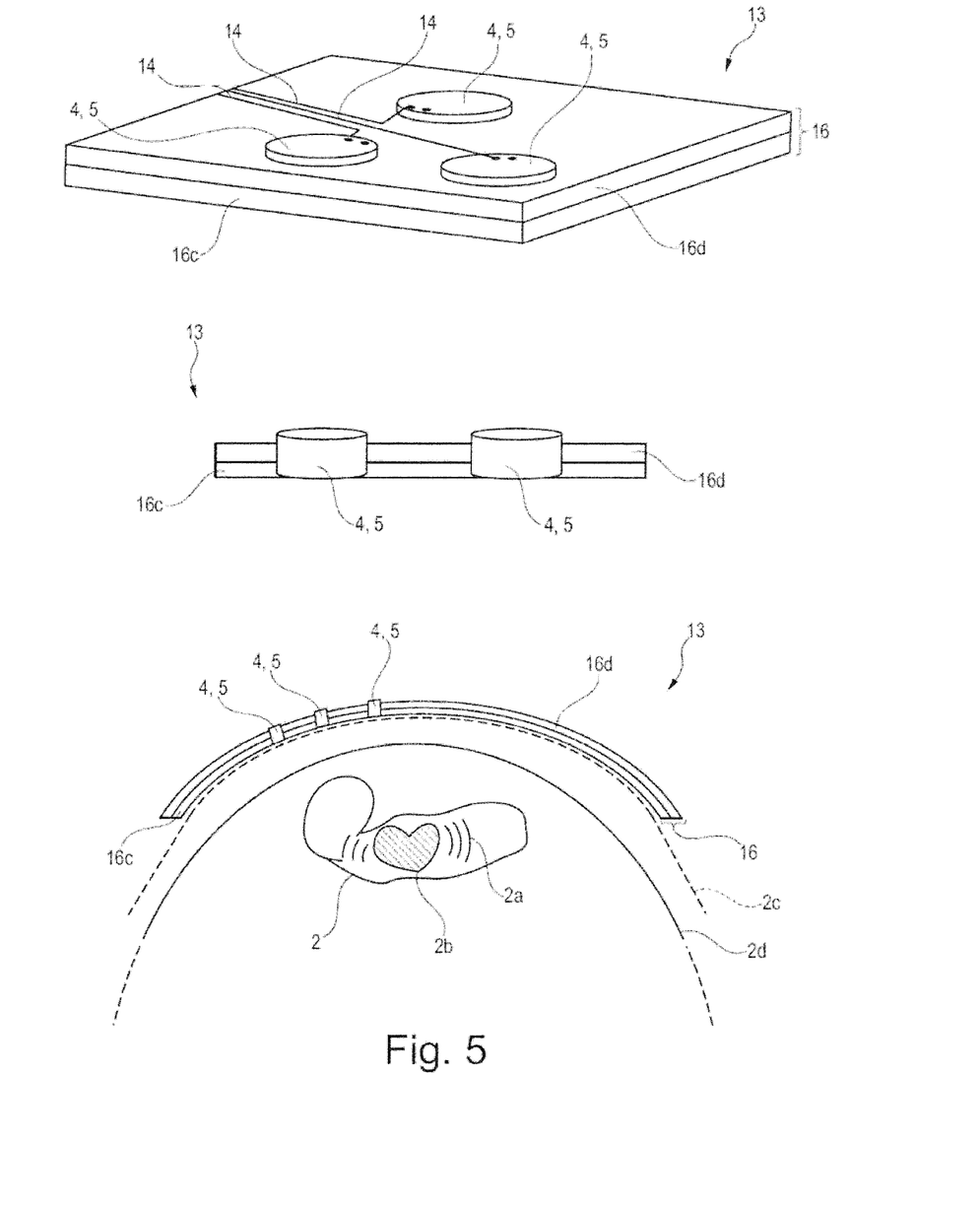
FIG. 5: an assembly of a transceiver unit 13 with a flexible substrate 16 suitable for application on a mother's womb 2c.

FIG. 5 details the assembly of an exemplary embodiment shown in FIG. 4, as well as its use. The flexible substrate 16 consists of a flexible plastic mat 16c and a flexible printed circuit board 16d onto which all wiring (for example, branch lines 14) is printed. The transceivers 4, 5 are set into both the flexible plastic mat 16c and the flexible printed circuit board 16d. The plastic mat 16c and the printed circuit board 16d are joined together in a watertight manner by gluing.

To monitor the heartbeat 2a of a fetus 2 inside an uterus 2d, the transceiver unit 13 is placed on the mother's womb 2c with the flexible plastic mat 16c facing towards the womb 2c. When the fetus 2 moves inside the uterus 2d, the heart 2h of the fetus 2 may move out of the detecting range of one of the transceivers 4, 5 and into the detecting range of another one of the transceivers 4, 5, of which only three are shown in FIG. 5 for clarity. The tracking module/arrangement 66 registers this intra-uterine movement and instructs the feedback module/arrangement 67 to power on the correct transceivers 4, 5 in order to ensure an uninterrupted detection of the heartbeat 2a.

Figure 6:
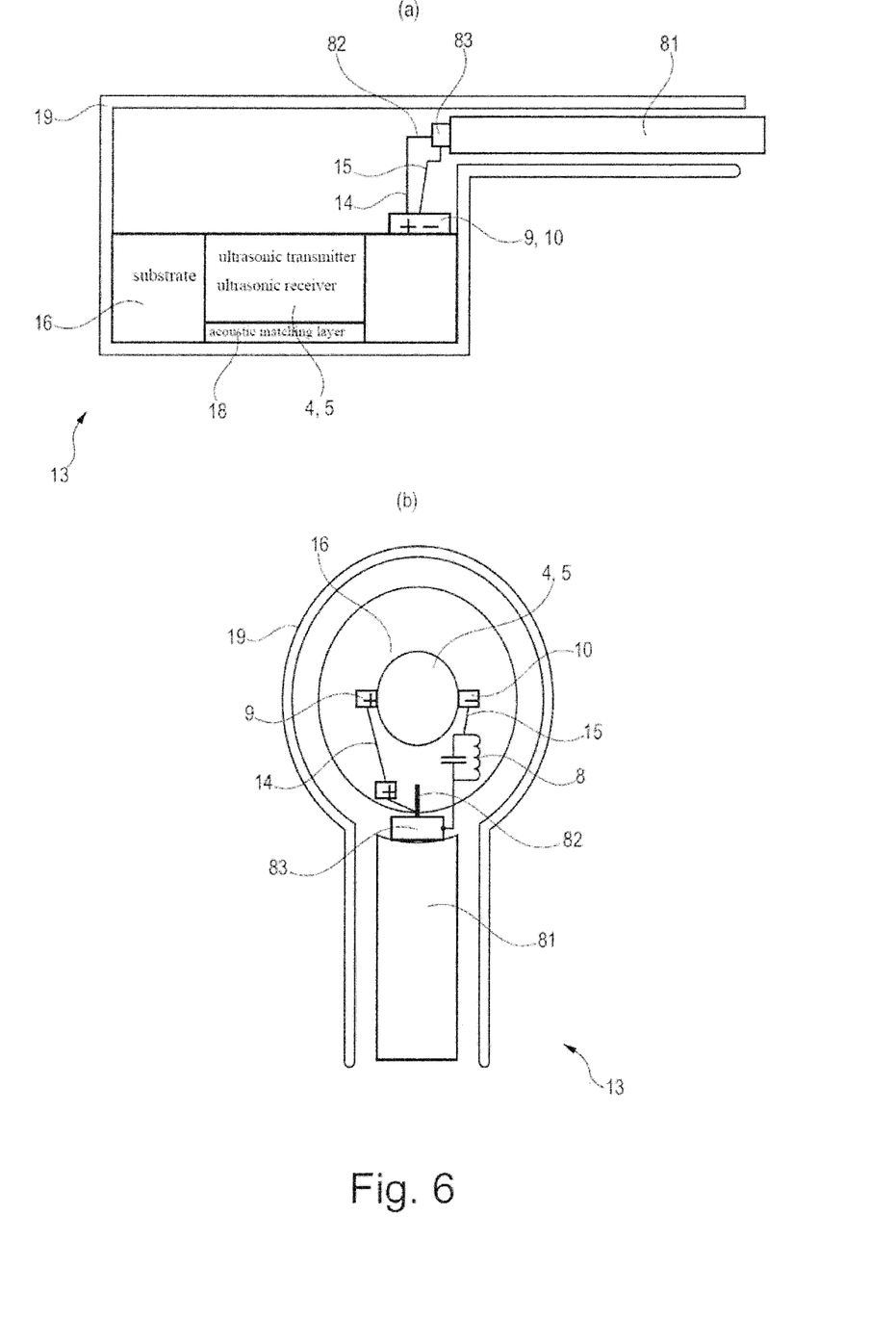
FIG. 6: a further exemplary embodiment of the transceiver unit 13 adapted for use on an adult patient 2.

FIG. 6 illustrates a further exemplary embodiment of a transceiver unit 13 that can be adapted for use on an adult patient 2. Sub-figure (a) shows a sectional side view, sub-figure (b) shows a top view.

Since an adult's heartbeat produces a much stronger signal, only one transceiver 4, 5 is required. The transceiver 4, 5 is set in a printed circuit board 16 inside a housing 19 and connected by an acoustic matching layer 18 to this housing 19. The first (positive, plus) terminal 9 of the transceiver 4, 5 is connected by a branch line 14 to the inner conductor 82 of the coaxial signal cable 81. The second (negative, minus) terminal 10 of the transceiver 4, 5 is connected by a branch line 15 to the outer conducting shield 83 of the coaxial signal cable 81. A standing wave trap 8 is installed between the second terminal 10 of the transceiver 4, 5 and the outer conducting shield 83.

Figure 7:
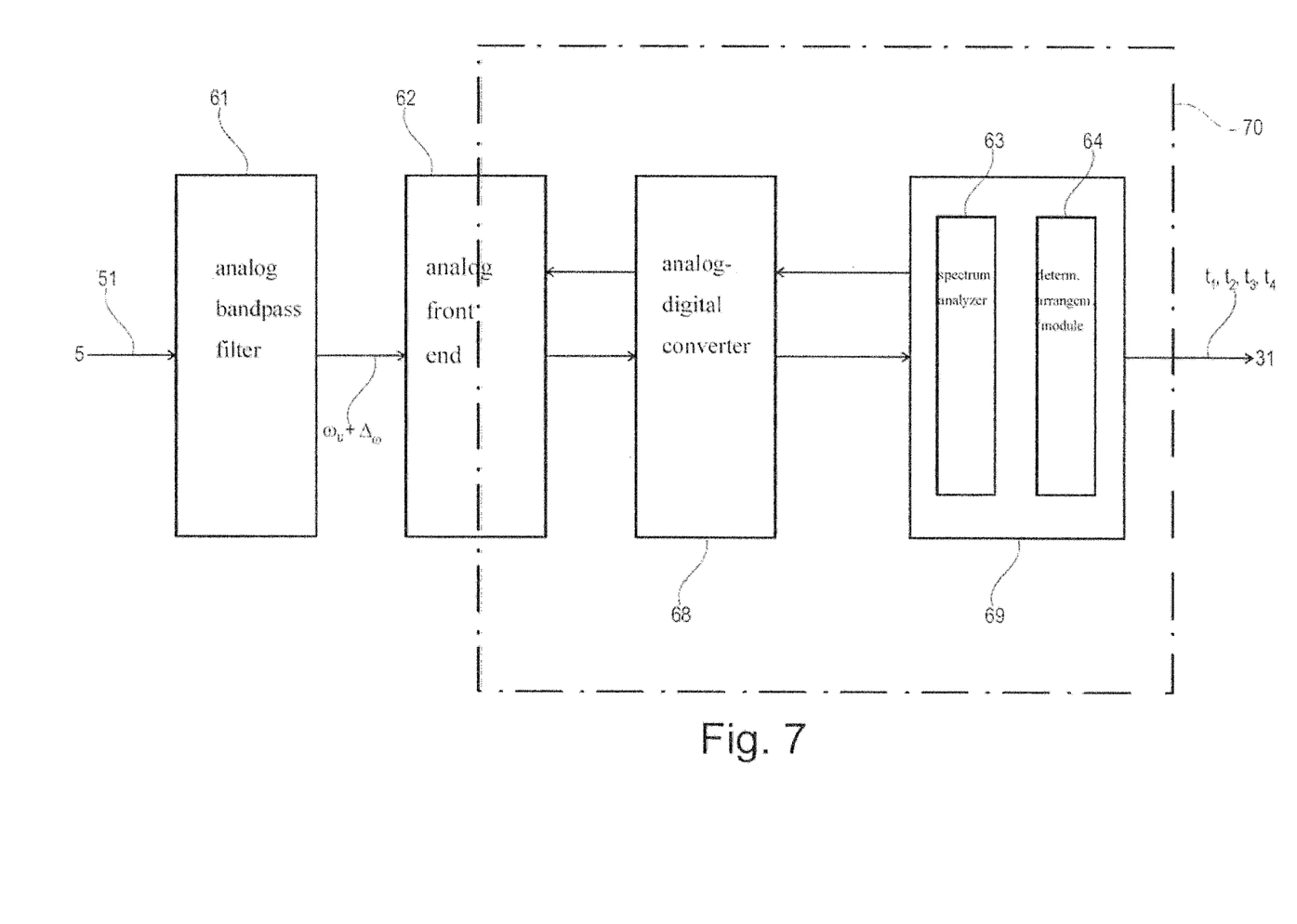
FIG. 7: an interfacing of the evaluating arrangement/module 6 with the receiver 5 and the trigger input 31 of the MRI apparatus 3.

FIG. 7 illustrates the interfacing of the evaluating module/arrangement 6 with the receiver 5 and the trigger input 31 of the MRI apparatus 3. The signal 51 from the receiver 5 first passes through the analog bandpass filter 61 that only lets frequencies in the range $\omega_U \pm \Delta\omega$ pass. The analog front end 62 receives, amplifies, demodulates and filters the signal 51 to signal 51a. The demodulation may also be performed in the digital domain downstream of the analog front end 62, as long as it is performed before the decomposition of the signal 51a into frequency components. The analog front end 62 is the entry and exit point of a microcontroller 70 that further comprises a combined analog-digital and digital-analog converter 68, as well as a digital signal processor 69 that implements the function of the spectrum analyzer 63 and the determining module/arrangement 64.

Figure 8:
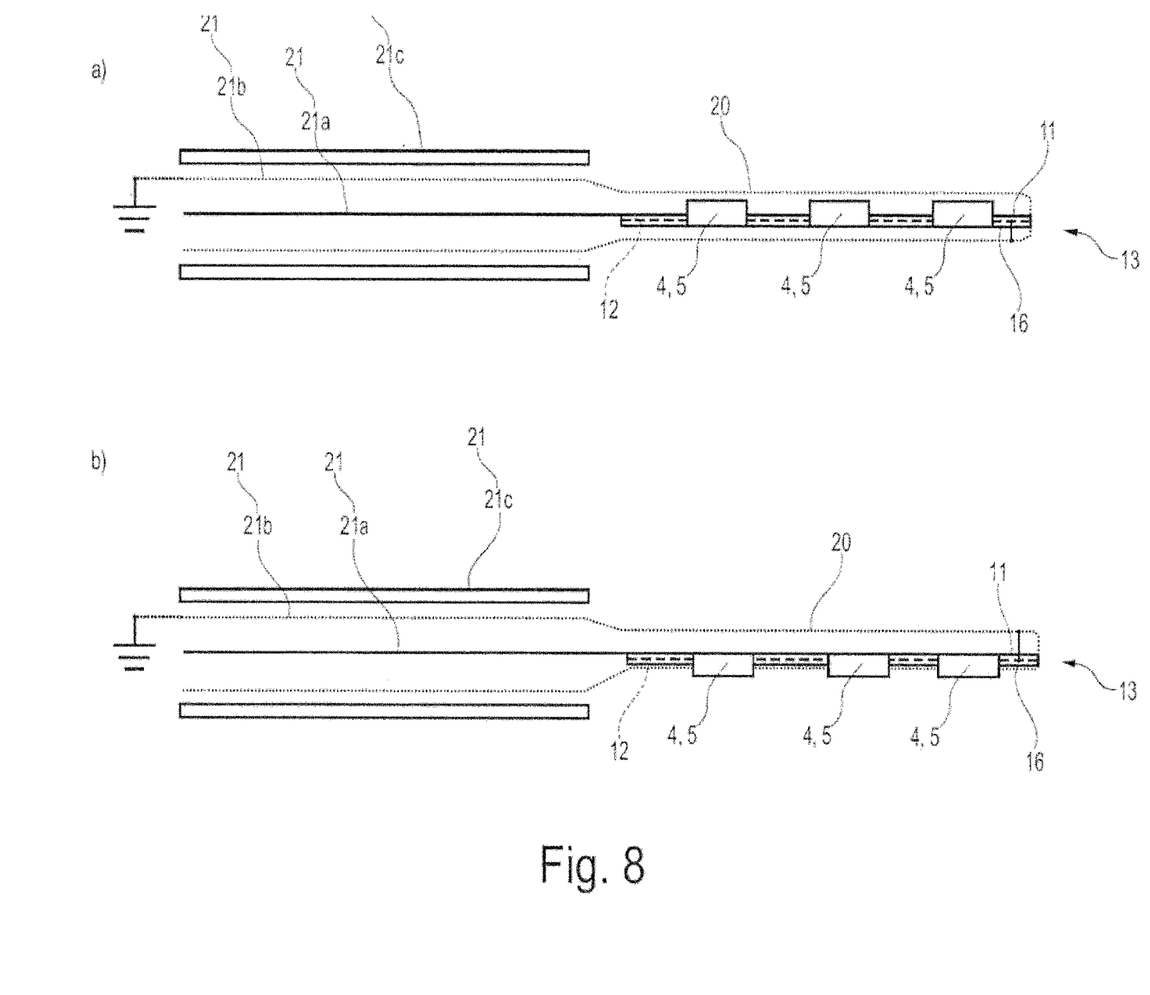
FIG. 8: a shielding 20 of the substrate 16, connected to a coaxial cable 21.

FIG. 8 shows a transceiver unit 13 according to an embodiment where the common dielectric substrate 16 onto which the transceivers 4, 5 are mounted is surrounded by a conductive shield 20. The transceiver unit 13 is connected to a coaxial cable 21 comprising an inner conductor 21a, a grounded outer conductor 21b that serves to shield the inner conductor 21a, and a plastic cladding 21c. The inner conductor 21a of the cable 21 is connected to the first common bus 11 on the substrate 16, while the outer conductor 21b of the cable 21 is connected to the shield 20. The shield 20 is in turn connected to the second common bus 12 on the substrate 16.

Two variants are shown in FIG. 8. FIG. 8a shows a first variant where the transceivers 4, 5 are completely covered by the shield 20. FIG. 8b shows a second variant where the transceivers 4, 5 protrude through the shield 20, so that the shield 20 does not impede the coupling of transmitted and reflected ultrasonic waves in any way.

Figure 9:
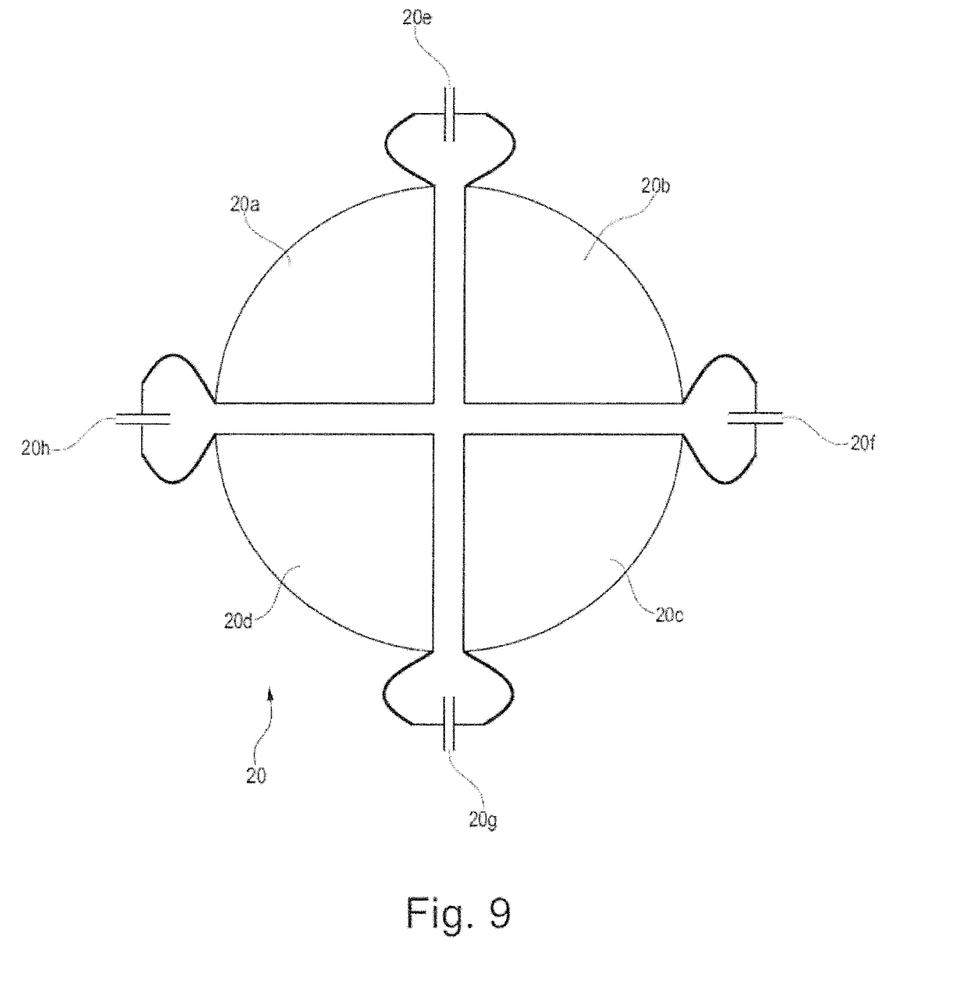
FIG. 9: a division of shield 20 into segments 20a-20d connected by capacitors 20e-20h.

FIG. 9 shows the division of a shield 20 into four segments 20a-20d. The segments are connected to each other via capacitors 20e-20h. Lower frequencies that are mainly relevant for the generation of eddy currents are blocked by the capacitors 20e-20h, so that the shield 20 does not heat up. Higher frequencies that have the potential to interfere with the measurement pass the capacitors, and are therefore shorted by the shield 20.

EXEMPLARY LIST OF REFERENCE SIGNS 1 device
2 patient (adult or fetus)
2a heartbeat of patient 2
2h heart of patient 2
2c mother's womb
2d uterus
3 MRI apparatus
4 ultrasonic transmitter
4a ultrasound transmitted by transmitter 4
5 ultrasonic receiver
5a ultrasound received by receiver 5
6 evaluating module/arrangement
7 display unit
8 standing wave trap
9 first terminal
10 second terminal
11 first common bus
12 second common bus
13 transceiver unit
14 branch lines to first common bus 11
15 branch lines to second common bus 12

16 substrate
16a, 16b top and bottom faces of substrate 16
16c flexible plastic mat of substrate 16
16d flexible printed circuit board of substrate 16
17a-17h groups of transceivers 4, 5
18 acoustic matching layer
19 housing
20 conductive shield
20a-20d segments of conductive shield 20
20e-20h capacitors between segments 20a-20d
21 cable to connect to common buses 11, 11a-h, and 12
21a, 21b concentric conductors of cable 21
21c plastic cladding of cable 21
31 trigger input of MRI apparatus 3
51 time-dependent signal from receiver 5
51a time-varying filtered Doppler signal derived from signal 51
51b frequency components of signal 51a
52 signal path from receiver 5 to spectrum analyzer 63
53a-53d window of interest, WOI
61 analog bandpass filter
62 analog front end
63 spectrum analyzer
64 determining module/arrangement
65 housing of evaluating module/arrangement 6
66 tracking module/arrangement
67 feedback module/arrangement
68 analog-digital converter
69 digital signal processor
70 microcontroller
81 coaxial cable
81a coil formed in coaxial cable 81
82 inner conductor of coaxial cable 81
83 outer conducting shield of coaxial cable 81
84 first coil formed in inner conductor 81
85 second coil formed in outer conducting shield 83
86 capacitor
100 system
A amplitude (time domain)/spectral power density ($\omega$ domain)
$b_1$, $b_2$, $b_3$, $b_4$ amplitudes of E wave maxima in signal 51
$m_a$, $m_b$, $m_d$. amplitudes of maxima in frequency component 51a
$m_e$, $m_f$, $m_g$, $m_h$ amplitudes of minima in frequency component 51a
t time
$\Delta t$ length of windows 53a-53d
$t_a$, $t_b$, $t_c$, $t_d$ moments of maxima in frequency component 51a
$t_e$, $t_f$, $t_g$, $t_h$ moments of minima in frequency component 51a
$t_0$ point in time for generation of diagram (b) in FIG. 2
$t_1$, $t_2$, $t_3$, $t_4$ moment of heartbeat 2a of patient 2
$\omega_G$ switching frequency of gradient field in MRI apparatus 3
$\omega_R$ radio frequency field in MRI apparatus 3
$\omega_U$ frequency of ultrasound 4a
$\Delta\omega$ maximum Doppler shift of ultrasound 5a

The invention claimed is:

1. A device for detecting a heartbeat of a patient, comprising
a transmitter which is configured to provide ultrasonic waves;
a receiver configured to receive Doppler-shifted ultrasonic waves;
a computer hardware analyzing apparatus coupled to the receiver and configured to evaluate a particular moment of the heartbeat of the patient based on a time-dependent signal obtained from the receiver, wherein the computer hardware analyzing apparatus comprises:
a spectrum analyzer configured to extract at least one time-varying frequency component from the time-dependent signal provided by the receiver, and
a computer processing module which configures a computer to evaluate the particular moment of the heartbeat based on a variation of the at least one frequency component in time; and
a transceiver device including at least one further transmitter and a plurality of further receivers, wherein:
each of the further receivers has a first output terminal and a second output terminal,
each of the first output terminals of at least two of the further receivers is connected by a first branch line to a first common bus, and
each of the second output terminals of the at least two of the further receivers is connected by a second branch line to a second common bus,
wherein a signal path between at least one of the further receivers and the spectrum analyzer comprises at least one standing wave trap configured to substantially block a radio frequency of a magnetic resonance imaging (MRI) apparatus, and
wherein the computer processing module configures the computer hardware analyzing apparatus to determine (i) a window of interest (WOI) in time from the variation of the at least one frequency component in time, and (ii) a moment when the time-dependent signal provided by the receiver assumes a maximum within the WOI as the particular moment of the heartbeat.

2. The device according to claim 1, wherein the heartbeat of the patient is detected during imaging using the magnetic resonance imaging apparatus, or a further imaging apparatus having a different modality.

3. The device according to claim 1, wherein the processing module configures the computer hardware analyzing apparatus to determine a further moment when the at least one frequency component assumes a further maximum as the particular moment of the heartbeat.

4. The device according to claim 3, wherein the processing module configures the computer hardware analyzing apparatus to determine the WOI as at least one of (i) a window of pre-set length around the further moment where the at least one frequency component assumes the further maximum, or (ii) a window that extends between at least two additional moments when the at least one varying frequency component assumes a minimum.

5. The device according to claim 1, wherein the further transmitter and the further receivers are mounted on a common dielectric substrate which includes at least one flexible portion.

6. The device according to claim 5, wherein the common dielectric substrate is at least partially surrounded by a conductive shield.

7. The device according to claim 6, wherein at least part of the conductive shield is grounded.

8. The device according to claim 7, wherein the first common bus and the second common bus are connected to at least two different concentric conductors of a cable, and wherein at least part of the conductive shield is grounded via an outermost one of the conductors of the cable.

9. The device according to claim 6, wherein at least part of the conductive shield is divided into a plurality of segments.

10. The device according to claim 9, wherein at least two of the segments are electrically connected via a capacitor.

11. The device according to claim 5, wherein the first common bus and the second common bus are at least one of (i) arranged on different faces of the common dielectric substrate, or (ii) interwoven along at least part of a signal path between at least one of the further receivers and the spectrum analyzer.

12. The device according to claim 1, wherein the transceiver comprises a plurality of further transmitters, and wherein the processing module comprises a tracking module which configures the computer hardware analyzing apparatus to determine which of at least one of the further transmitters or the further receivers cover a present position of the heart of the patient, so that the Doppler-shifted ultrasonic waves are registerable by at least one of the further receivers and evaluated using the processing module.

13. The device according to claim 12, wherein the processing module comprises a feedback module which configures the computer hardware analyzing apparatus to control an operation of the plurality of transmitters, and wherein the feedback module configures the computer hardware analyzing apparatus to power on only particular ones of the particular transmitters which have been identified to cover the present position of the heart of the patient using the tracking module.

14. The device according to claim 1, wherein the at least one standing wave trap is formed from a coaxial cable having an inner conductor and an outer conducting shield, wherein the coaxial cable is wound to a coil so that a first coil is formed in the inner conductor and a second coil is formed in the conducting shield, and wherein the second coil provided in the outer conducting shield is bridged by a capacitor that forms the at least one standing wave trap in combination with the second coil provided in the outer conducting shield.

15. The device according to claim 1, wherein the signal path comprises a plurality of standing wave traps such that, in the radio frequency field of the MRI apparatus, the time-dependent signal travels at most a quarter of a wavelength corresponding to the radio frequency before traversing a first one or a further one of the plurality of standing wave traps.

16. The device according to claim 1, wherein a signal path between the at least one of the further receivers and the spectrum analyzer comprises a bandpass filter that rejects a switching frequency of a gradient field of an MRI apparatus and a radio frequency of the MRI apparatus.

17. The device according to claim 1, wherein at least part of the processing module is shielded by a housing that comprises a conductive carbon fiber.

18. A system comprising:
   a magnetic resonance tomography magnetic resonance imaging (MRI) apparatus; and
   a device for detecting a heartbeat of a patient, comprising
      i. a transmitter which is configured to provide ultrasonic waves,
      ii. a receiver configured to receive Doppler-shifted ultrasonic waves, and
      iii. a computer hardware analyzing apparatus coupled to the receiver and configured to evaluate a particular moment of the heartbeat of the patient based on a time-dependent signal obtained from the receiver, wherein the computer hardware analyzing apparatus comprises:
         a spectrum analyzer configured to extract at least one time-varying frequency component from the time-dependent signal provided by the receiver, and
         a processing module which configures the computer hardware analyzing apparatus to evaluate the particular moment of the heartbeat based on a variation of the at least one frequency component in time, and
      iv. a transceiver apparatus including at least one further transmitter and a plurality of further receivers, wherein:
         each of the further receivers has a first output terminal and a second output terminal,
         each of the first output terminals of at least two of the further receivers is connected by a first branch line to a first common bus, and
         each of the second output terminals of the at least two of the further receivers is connected by a second branch line to a second common bus,
      wherein a signal path between at least one of the further receivers and the spectrum analyzer comprises at least one standing wave trap configured to substantially block a radio frequency of the MRI apparatus, and
      wherein the processing module configures the computer hardware analyzing apparatus to determine (i) a window of interest (WOI) in time from the variation of the at least one frequency component in time, and (ii) a moment when the time-dependent signal provided by the receiver assumes a maximum within the WOI as the particular moment of the heartbeat, and
   wherein a trigger input of the MRI apparatus that triggers an image acquisition is coupled to the processing module of the device to receive the particular moment of the heartbeat of the patient, so that image acquisition is triggered at that moment.

19. A device for detecting a heartbeat of a patient, comprising
   a transmitter which is configured to provide ultrasonic waves;
   a receiver configured to receive Doppler-shifted ultrasonic waves; and
   a computer hardware analyzing apparatus coupled to the receiver and configured to evaluate a particular moment of the heartbeat of the patient based on a time-dependent signal obtained from the receiver, wherein the computer hardware analyzing apparatus comprises:
      a spectrum analyzer configured to extract at least one time-varying frequency component from the time-dependent signal provided by the receiver, and
      a computer processing module which configures a computer to evaluate the particular moment of the heartbeat based on a variation of the at least one frequency component in time,
   wherein the computer processing module configures the computer hardware analyzing apparatus to determine (i) a window of interest (WOI) in time from the variation of the at least one frequency component in time, and (ii) a moment when the time-dependent signal provided by the receiver assumes a maximum within the WOI as the particular moment of the heartbeat, and
   wherein the processing module configures the computer hardware analyzing apparatus to determine:
      a further moment when the at least one frequency component assumes a further maximum as the particular moment of the heartbeat, and the WOI as at least one of (i) a window of pre-set length around the further moment where the at least one frequency component assumes the further maximum, or (ii) a window that extends between at least two additional moments when the at least one varying frequency component assumes a minimum.

20. A device for detecting a heartbeat of a patient, comprising
  a transmitter which is configured to provide ultrasonic waves;
  a receiver configured to receive Doppler-shifted ultrasonic waves;
  a computer hardware analyzing apparatus coupled to the receiver and configured to evaluate a particular moment of the heartbeat of the patient based on a time-dependent signal obtained from the receiver, wherein the computer hardware analyzing apparatus comprises:
    a spectrum analyzer configured to extract at least one time-varying frequency component from the time-dependent signal provided by the receiver, and
    a computer processing module which configures a computer to evaluate the particular moment of the heartbeat based on a variation of the at least one frequency component in time; and
  a transceiver device including at least one further transmitter and a plurality of further receivers, wherein:
    each of the further receivers has a first output terminal and a second output terminal,
    each of the first output terminals of at least two of the further receivers is connected by a first branch line to a first common bus, and
    each of the second output terminals of the at least two of the further receivers is connected by a second branch line to a second common bus,
  wherein the transceiver comprises a plurality of further transmitters, and wherein the processing module comprises a tracking module which configures the computer hardware analyzing apparatus to determine which of at least one of the further transmitters or the further receivers cover a present position of the heart of the patient, so that the Doppler-shifted ultrasonic waves are registerable by at least one of the further receivers and evaluated using the processing module; and
  wherein the computer processing module configures the computer hardware analyzing apparatus to determine (i) a window of interest (WOI) in time from the variation of the at least one frequency component in time, and (ii) a moment when the time-dependent signal provided by the receiver assumes a maximum within the WOI as the particular moment of the heartbeat.

21. A device for detecting a heartbeat of a patient, comprising
  a transmitter which is configured to provide ultrasonic waves;
  a receiver configured to receive Doppler-shifted ultrasonic waves; and
  a computer hardware analyzing apparatus coupled to the receiver and configured to evaluate a particular moment of the heartbeat of the patient based on a time-dependent signal obtained from the receiver, wherein the computer hardware analyzing apparatus comprises:
    a spectrum analyzer configured to extract at least one time-varying frequency component from the time-dependent signal provided by the receiver, and
    a computer processing module which configures a computer to evaluate the particular moment of the heartbeat based on a variation of the at least one frequency component in time,
  wherein the computer processing module configures the computer hardware analyzing apparatus to determine (i) a window of interest (WOI) in time from the variation of the at least one frequency component in time, and (ii) a moment when the time-dependent signal provided by the receiver assumes a maximum within the WOI as the particular moment of the heartbeat, and
  wherein at least part of the processing module is shielded by a housing that comprises a conductive carbon fiber.

* * * * *